(12) United States Patent
Katz et al.

(10) Patent No.: US 6,580,944 B1
(45) Date of Patent: Jun. 17, 2003

(54) METHOD AND APPARATUS FOR DIAGNOSING SLEEP BREATHING DISORDERS WHILE A PATIENT IN AWAKE

(75) Inventors: Richard A. Katz, East Lyme, CT (US); Michael S. Lawee, Marblehead, MA (US); Anthony Kiefer Newman, Woburn, MA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 09/724,402

(22) Filed: Nov. 28, 2000

(51) Int. Cl.[7] ............................................. A61B 5/0472
(52) U.S. Cl. ....................................... 600/513; 600/529
(58) Field of Search ................................. 600/513, 529, 600/532, 533, 534, 535, 536, 537, 538, 539, 540, 301

(56) References Cited

U.S. PATENT DOCUMENTS 5,769,084 A * 6/1998 Katz et al.

* cited by examiner

Primary Examiner—Scott M. Getzow
(74) Attorney, Agent, or Firm—James M. Kasischke; Michael F. Oglo; Jean-Paul Nasser

(57) ABSTRACT

An apparatus and method for identifying the timing of the onset of and duration of an event characteristic of sleep breathing disorder while a patient is awake. Chaotic processing techniques analyze data concerning a cardio-respiratory function, such as nasal air flow. Excursions of the resulting signal beyond a threshold provide markers for delivering the average repetition rate for such events that is useful in the diagnosis of obstructed sleep apnea and other respiratory dysfunctions.

30 Claims, 5 Drawing Sheets

METHOD AND APPARATUS FOR DIAGNOSING SLEEP BREATHING DISORDERS WHILE A PATIENT IN AWAKE

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION (1) Field of the Invention

This invention is generally related to methods and apparatus for performing medical diagnoses and particularly to a method and apparatus for enabling the diagnosis of sleep breathing disorders or other physiological respiratory dysfunction while the patient is awake.

(2) Description of the Prior Art

Sleep breathing disorders and other physiological respiratory dysfunctions in humans constitute an area requiring diagnosis. One such area is called obstructive sleep apnea or sleep disorder breathing. Within the pediatric, infant and newborn population the incidence of apparent life threatening events, sudden infant death syndrome and sleep disorder breathing have all been well documented. Sleep apnea also affects over 25% of apparently healthy adults age 55 and older. Sleep apnea contributes to daytime fatigue, increased work place accidents and a number of cardiovascular disorders. The need for a relatively easily implemented procedure exists to provide efficient methods and procedures for diagnosing these various physiological respiratory dysfunctions.

U.S. Pat. No. 4,982,738 to Griebel discloses a diagnostic apnea monitor system that records snoring and respiration sounds made by a patient as well as the patient's heart rate while the patient is sleeping. Signals indicative of snoring sounds and the time intervals therebetween are produced from the recorded respiration. The system generates a first respiration disturbance index representing the number of intervals per hour between episodes of snoring. An average heart rate is also generated in response to the patient's recorded second respiration disturbance index representing the number of episodes per hour in which the patient's heart rate remained at 90% to 109% of its average rate is calculated. A physician then evaluates the first and second disturbance indices to determine whether obstructive sleep apnea is indicated.

U.S. Pat. No. 5,101,831 to Koyama et al. discloses a system for discriminating a sleep state and selectively waking a patient. This system provides variation indices representing the variation of a biological signal on the basis of a first variation amount denoting a tendency of a time series of measured biological signal to increment from the starting time of the measurement and a second variation amount denoting the temporal variation of the biological signal. These signals enable the discrimination of different sleep states, namely the NREM and REM sleep states, on the basis of the distribution of the density of the variation indices exceeding a predetermined threshold.

U.S. Pat. No. 5,105,354 to Nishimura provides a method and apparatus for correlating respiration and heartbeat variability and particularly a method for forecasting sudden infant death syndrome by investigating the correlation between respiration and heart beat in a normal state and a sleep-apnea state of a newborn. In essence the system detects respiratory information, produces an envelope indicative of the respiration information and samples the envelope to produce a fast Fourier transform spectrum of the envelope information. Simultaneously the system detects cardio-electric information in the form of an EKG, detects the peak value and calculates a sequential R—R interval series that is fast Fourier transformed into a spectrum of the R—R interval variation. These two complex conjugations are multiplied and, through a fast Fourier transform, analyzed to calculate a correlation between respiration and heart beat that can then be evaluated to identify the state just before the normal state of a newborn will convert to the state of sleep apnea and forecast sudden death syndrome.

U.S. Pat. No. 5,385,144 to Yamanishi et al. discloses a respiration diagnosis apparatus that distinguishes between obstructive sleep apnea and central apnea automatically. An analog signal processor generates pulse wave signals based on light received from a light emitting means and passing through or reflecting off living tissue. A pulse wave line analog signal processor extracts change components of a base line of the generated pulse wave signal. A master microcomputer distinguishes between obstructive apnea and central apnea on the basis of the extracted pulse wave base line change components.

U.S. Pat. No. 5,398,682 to Lynn discloses a method and apparatus for the diagnosis of sleep apnea utilizing a single interface with a human body part. More specifically, the diagnosis identifies the desaturation and resaturation events in oxygen saturation of a patient's blood. The slope of the events is determined and compared against various information to determine sleep apnea.

It has also been recognized that cardio and respiratory signals are signals of non-linear dynamical systems. U.S. Pat. No. 5,404,298 to Wang et al. and U.S. Pat. No. 5,453,940 to Broomhead et al. disclose dynamical system analyzers or chaos analyzers useful in determining characteristics based upon such dynamical system signals. Additional information on the use of chaos is contained in Strogatz, Steven H., *Non-linear Dynamics in Chaos*, Reading, Mass., Addison Wesley Publishing Company, 1994, p. 379.

U.S. Pat. No. 5,769,084 filed by the same inventors as this application, discloses an apparatus and method for identifying the timing of the onset of and duration of an event characteristic of sleep-breathing disorder during a conventional overnight sleep study. Chaotic processing techniques analyze data concerning one or more cardio-respiratory functions, such as nasal airflow, chest wall effort, oxygen saturation, heart beat and heart activity. Excursions of the resulting signal beyond a threshold provide markers for the timing of such an event that is useful in the diagnosis of obstructed sleep apnea and other respiratory dysfunctions.

Conventional sleep studies require significant resources. Generally they are conducted in special facilities. One patient is located in one room for the night and typically arrives about 8:00 PM and leaves about 6:00 am. At least two trained technicians generally are present for the duration of each test. They attach the various sensors to the head, chest, arms and legs and then monitor the various signals from different patients. The results as multichannel charts and observed events are then reviewed by one or two physicians of different specialties in order to determine the existence of sleep apnea or other respiratory dysfunction conditions. Given this requirement, conventional sleep studies require significant physical plant assets that are not available for other purposes. In addition, the diagnosis is labor intensive.

Katz et al., "A Practical Non-Linear Method for Detection of Respiratory and Cardiac Dysfunction in Human Subjects", SPIE Vol. 2612, Page 189 (1995) hypothesizes the possibility of making a diagnosis while a patient is awake. The paper presents no quantitative results and merely plots a temporal signal dependent on a physiological function. What is needed is a diagnostic test that can screen patients sleeping disorders or other respiratory dysfunctions while the patient is awake thereby to eliminate the requirement for conventional sleep studies in many patients. Notwithstanding the existence of the foregoing prior art, the current conventional approach for diagnosing sleep apnea continues to be the diagnosis of choice.

SUMMARY OF THE INVENTION

Therefore it is an object of this invention to provide a method and apparatus for facilitating the diagnosis of sleep breathing disorders while a patient is awake.

Another object of this invention is to provide a method and apparatus for generating markers that identify the onset and duration of an event characteristic of a sleep breathing disorder while a patient is awake.

In accordance with this invention, a cardio-respiratory function is monitored over time while a patient is awake. A digitized time series representation of each monitored cardio-respiratory function is generated. Chaotic processing of the corresponding time series representation yields a processed signal. Excursions of this signal beyond a corresponding threshold value indicate the time of an onset of an event and its duration.

BRIEF DESCRIPTION OF THE DRAWINGS

The appended claims are intended to point out with particularity and to claim distinctly the subject matter of this invention. The various objects, advantages and novel features of this invention will be more fully apparent from a reading of the following detailed description in conjunction with the accompanying drawings in which like reference numerals refer to like parts, and in which:

DESCRIPTION OF THE PREFERRED EMBODIMENT

Figure 1:
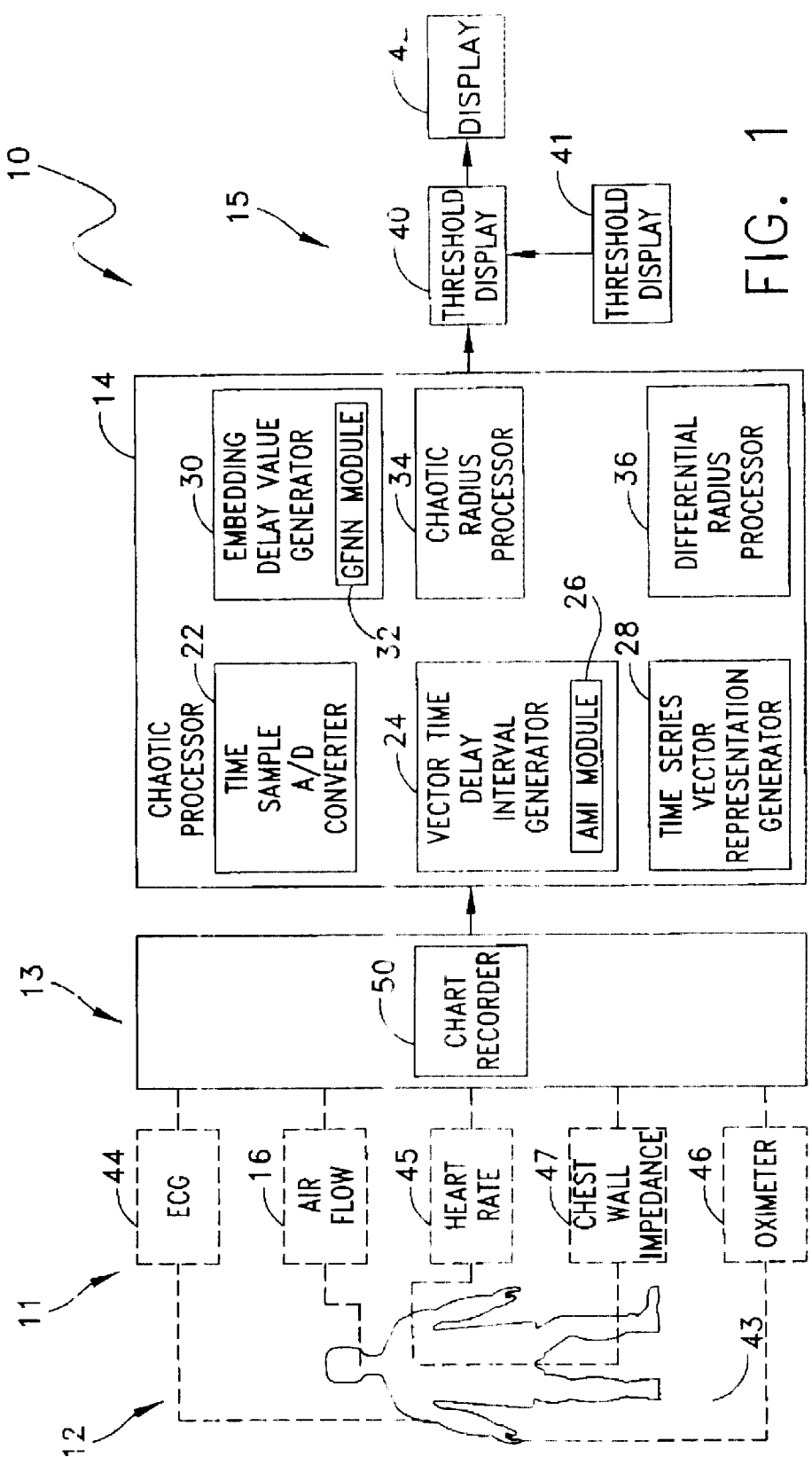
FIG. 1 depicts a patient and, in block diagram form, apparatus for implementing this invention.

Apparatus 10 embodying this invention includes one or more monitors 11, each of which monitors at least one cardio-respiratory function of a patient 12 over time. Each monitor 11. produces signals that a selector 13 can convey to a chaotic processor 14 that converts each selected signal into a time series representation of the monitored cardio-respiratory function and then generates a signal for that function based upon chaotic processing of the time series representation. An output then identifies as a marker each excursion of the signal beyond a corresponding threshold value thereby to indicate the timing of the onset of an event and its duration. FIG. 1 discloses specific embodiments of the monitors 11, chaotic processor 14 and output 15. As shown the selector 13 could act as a multiplexer or switch to sample each of these signals in seriatim. It will be apparent that the use of the selector is for purposes of explanation only. If the apparatus is designed to monitor only one function, the selector 13 can be eliminated.

If on-line results are required and multiple functions are monitored, the components of the chaotic processor 14 could be duplicated either by incorporating multiple chaotic processors or by time sharing programs within the single chaotic processor in a manner synchronized by the selection of signals and known in the art.

One of the monitors 11 in FIG. 1 is an air flow monitor 16 that monitors oral nasal airflow. Any of a number of different flow and pressure transducer-based monitors can be used to provide a signal that accurately models the air flow from the patient 12. The output of the air flow monitor 16 may generate a strip chart and the function of the selector 13 could be provided by apparatus that automatically or with manual intervention provides an input to a digital-to-analog converter or otherwise enables the signal to be submitted into the chaotic processor in an analog form. Alternatively and preferably, the analog signals from the air flow monitor 16 could be digitized immediately for storage in a local memory.

Figure 2:
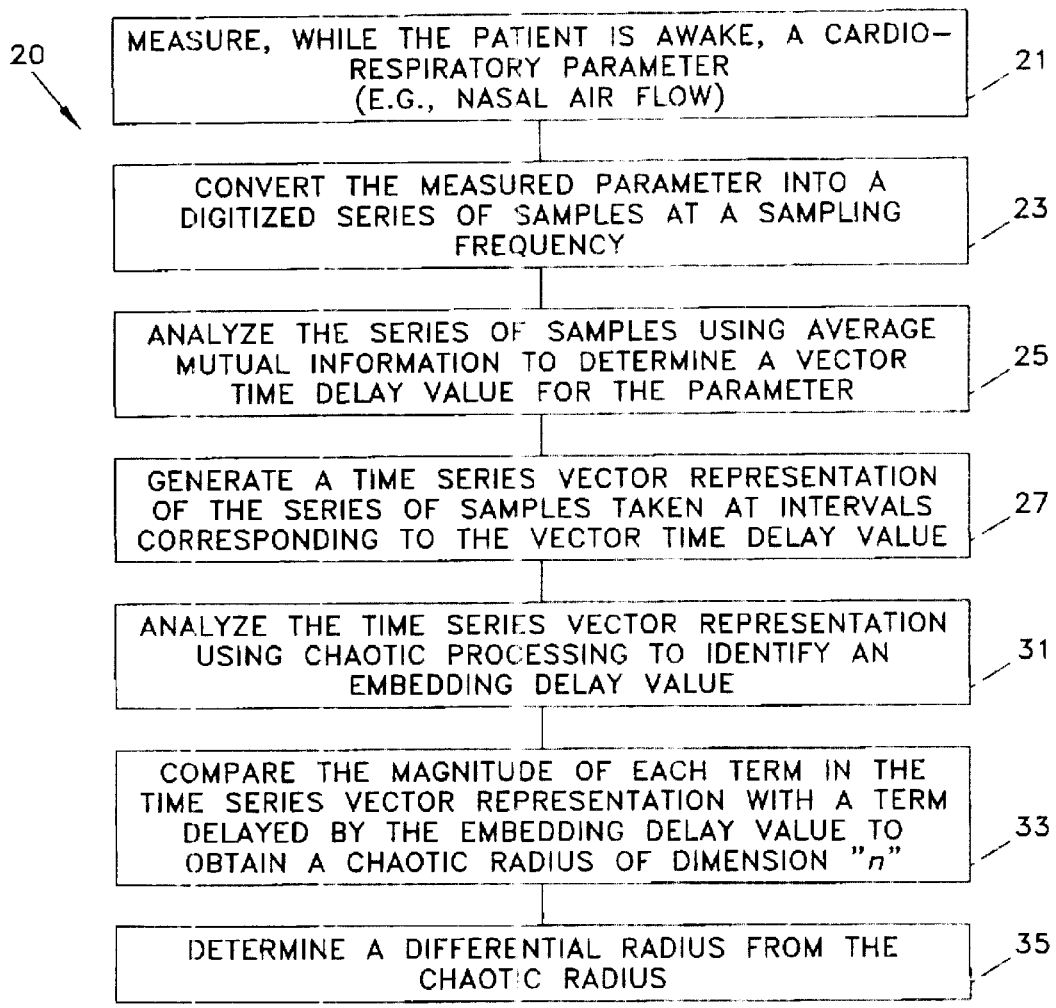
FIG. 2 is a flow chart representing the method in accordance with this invention employed by the apparatus in FIG. 1.

Before discussing the process of a signal from one of the monitors 11 and their respective signals it will be helpful to review the operation of the chaotic processor 14. Essentially in accordance with one aspect of this invention, the chaotic processor 14 converts an analog signal from a monitor 11 into a chaotic radius signal and a differential radius signal. FIG. 2 depicts the steps in one method for analyzing such a signal to determine the timing of the onset of an event characteristic of a sleep breathing disorder and its duration. Particularly, as an initial step, the system uses the signal from the oral-nasal air flow monitor 16 to measure nasal air flow as a cardio-respiratory function. This measurement is made while the patient is in a comfortable position and is awake. The measurement may last for any arbitrary time. It is expected that measurements will be made for up to one hour or so. A time sample A/D converter 22 in the chaotic processor 14 converts the measured function into a digitized time series of samples of the monitored function at a sampling frequency.

The sampling frequency must be selected to provide adequate sampling so that the following steps in the process will have sufficient data for providing reliable results with a reasonable temporal resolution. Oversampling is preferable to undersampling although this will increase the burdens of the processing time and complexity. It has been found that the minimum sampling frequency ought to be greater than the greatest frequency of physiologic relevance with respect to the monitored cardio-respiratory function. As a general rule, a sampling frequency of two to five times the Nyquist sampling frequency for linear signals provides good results. A sampling frequency between 10 Hz and 40 Hz provides adequate sampling for nasal air flow. Sampling rates above 40 Hz have been found to be effective for monitoring other non-linear physiological parameters. Still referring to FIGS. 1 and 2, the converter 22 and step 23 produce a digitized representation of the incoming cardio-respiratory function signal in the form of a scalar time series having the general form:

$$v(n)=v(t+ndt) \qquad (1)$$

where "t" is the start time for the diagnosis, "dt" is the sample interval (e.g., 0.10 seconds at a 10 Hz sampling frequency) and "n" is the sample number and n=1, 2, 3, . . . N.

A vector time delay interval generator 24 in FIG. 1 processes this scalar time series to determine an interval at which a series of vectors should be generated. This process can use several known techniques. Step 25 in FIG. 2 depicts a preferred alternative that uses a known process based upon average mutual information (AMI), represented by an AMI module 26 in FIG. 1, to determine the vector time delay. As known, average mutual information quantitates the information theoretic properties of chaotic systems. More specifically, average mutual information indicates how much information exists in the form of a time series, such as shown in Equation 1, about the measurement of that signal and shown in FIG. 1 concerning the measurement of that signal at a time Tdt later. That is, a time series v(n) for average mutual information indicates how much information will be available to predict the voltage level at a time Tdt later, i.e., the value v(n+T). Average mutual information processes distribute the measurements v(n) and v(n+T) over the set of measured data and determine the joint distribution of measurements of these two quantities. The first of these distributions is P(v(n)), the second is P(v(n+T), and the third is P(v(n), v(n+T)). The mutual information between these measurements is:

$$\ln\left[\frac{P(v(n), v(n+T))}{P(v(n))P(v(n+T))}\right] \quad (2)$$

where "ln" is the natural logarithm. For N observations, the average over all measurements is the AMI given by:

$$AMI = \sum_{n=1}^{N}\left[P(v(n), v(n+T))\ln\frac{P(v(n), v(n+T))}{P(v(n))P(v(n+T))}\right] \quad (3)$$

For independent measurements, each term in the above sum vanishes due to factorization of the joint probability P(a,b)=P(a)P(b). For the case T=0, I(0) is large because there is full knowledge of the measurements. Generally, however, I(T) will be greater than zero. The objective becomes determining an intermediate value of T that will preserve the information in the system without overburdening the process. With average mutual information, one approach is to choose the value for T that corresponds to the first minimum of I(T), although any value of T near the first minimum should suffice. As will be apparent the value of T can be any arbitrary number. Normally, the value will be refined so that it corresponds to an integer multiple of the sampling integral established in the converter 22.

Once the value T has been obtained, step 27 in FIG. 2 uses a time series vector representation generator 28 in the chaotic processor 14 to convert the digitized samples into a time series vector representation that has a sampling interval of T. Each vector points to the scalar value at an interval "T" later. More specifically the time series vector generator 28 in FIG. 1 operating in accordance with step 27 in FIG. 2 generates a d-dimensional set of vectors from a sequence of fixed vector time delays, T, in the form:

$$y(n)=[v(n), v(n+T), v(n+2T), \ldots v(n+(d-1))T] \quad (4)$$

where:

v(n) is the original time series datum at time index n;

v(n+T) is datum from the same time series offset in the positive direction by the vector time delay interval T;

v(n+2T) is datum from the same time series offset in the positive direction by the vector time delay interval 2T;

v(n+d−1)T is the datum offset by the vector delay interval (d−1)T where d is an embedding dimension to be obtained from an embedding delay value generator 30 in FIG. 1 as it processes step 31 in FIG. 2; and n is an index number for time series datum where n=1, 2, 3 . . . N and the maximum number of indices. N, may be selected to be any arbitrary large value. Typical values are 900 or greater.

These time delays are presented as having a positive direction. As apparent, they also can be taken as having a negative direction.

The resulting time series vector is then analyzed to determine a minimum embedding function, "d". As with respect to the generation of the vector time delay interval, alternate approaches are available for determining the embedding delay value. A preferred approach that has produced reliable results utilizes a known "global false nearest neighbor (GFNN)" process that is implemented in the generator 30 by an GFNN module 32. Basically this process is based upon the concept that when points of higher dimension are projected down to a space of lower dimension, there are overlapping orbits in the low dimension space such that if the process were reversed and given space were projected to a higher dimension it could be reasonably expected that neighboring points along a trajectory would separate. Basically the process starts with a first dimension, unfolds the time series vector representation to higher and higher dimensions while keeping track of the percentage of nearest neighbors that spread apart at each integer increase of dimension. When the quality of the predictions or motions of neighbors become independent of the dimensions, the resulting delay for one representation to the other producing the desired result constitutes the minimum embedding value.

More specifically the process determines the dimension "d" with points made out of the vector representation in which the nearest neighbors ynn(n) of the point y(n) is given by:

$$ynn(n)=[vnn(n), vnn(n+T) \ldots vnn(n+(d-1)T] \quad (5)$$

The process determines whether or not these points remain near in dimension (d+1), whether vector y(n) is augmented by a component v(n+dT) and ynn(n) is augmented by vnn(n+dT). For small distances the neighbors are true neighbors. For large distances false neighbors exist. When the percentage of false neighbors drops to zero, the resulting delay is the minimum embedding dimension or delay value.

Once the minimum embedding delay value has been determined, step 33 in FIG. 2 and a chaotic radius processor 34 in FIG. 1 compare the magnitude of each term in the time series vector representation with a term delayed by the embedding delay value to obtain a chaotic radius for each term. In general terms, the chaotic radius (r) for n dimensions is given by:

$$r = \sqrt[n]{X(t)^2 + X(t+p)^2 + \ldots + X(t+(n-1)p))^2} \quad (6)$$

The chaotic radius processor 34 in FIG. 1 effectively plots the scalar value of each point in the vector for some value of n>1.

Figure 3:
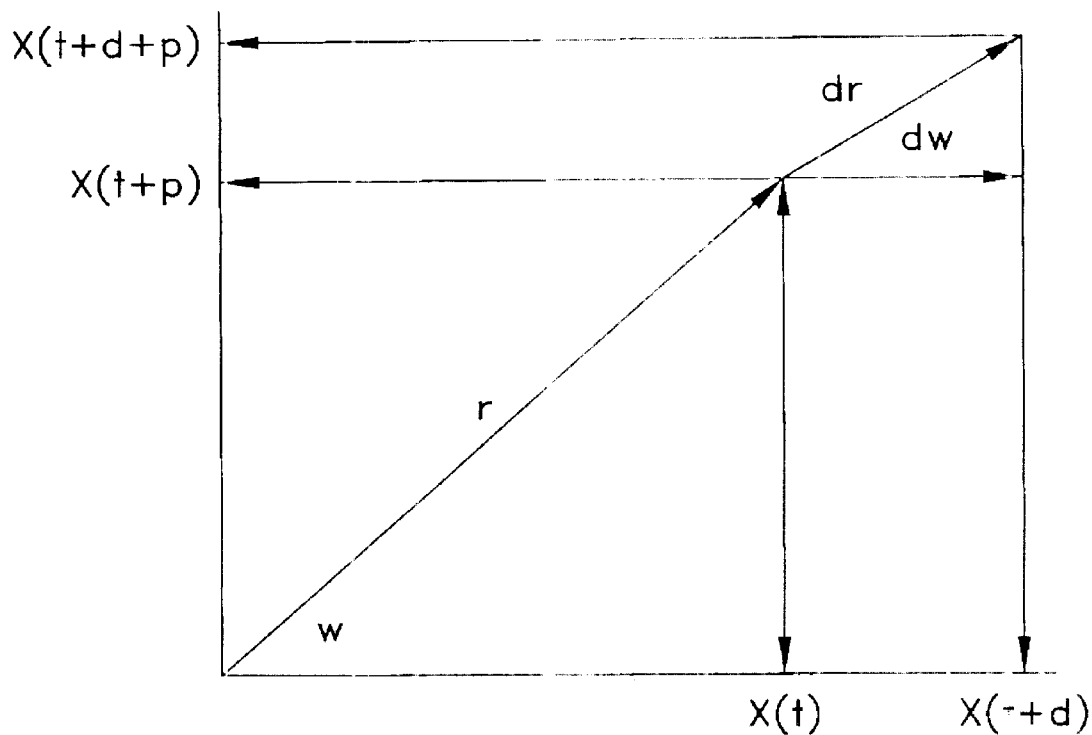
FIG. 3 is a diagram useful in understanding the operation of the apparatus and methods of FIGS. 1 and 2.

FIG. 3 depicts a solution for n=2. On a horizontal scale and a vertical scale, X(t), and X(t+p) represent the component magnitudes of the vector at time "t", points X(t+d) and X(t+d+p) respectively represent the change in magnitude between two successive points at "t" and at (t+d). Consequently the chaotic radius (r) for n=2 is given by:

$$r = \sqrt{X(t)^2 + X(t+p)^2} \quad (7)$$

It will be further evident that the differential radius (dr) can be determined by:

$$dr = \sqrt{[[X(t+d) - X(t)]^2 + [X(t+d+p) - X(t+p)]^2} \quad (8)$$

or by $$dr = r(i+1) - r(i) \quad (9)$$

Step 35 in FIG. 2 and a differential radius processor 36 in FIG. 1 compute, for each vector in the time series vector representation, a corresponding differential radius, dr, according to either of the foregoing alternatives.

Referring again to FIG. 1, the chaotic radius or the differential radius can transfer from the chaotic radius processor 34 or differential radius processor 36 to a threshold detector 40 in the output 15. A threshold selector 41 can be adjusted for the signal corresponding to chaotic radius or differential chaotic radius for different cardio-respiratory functions in order to provide, on a display 42, a representation of the chaotic radius or differential chaotic radius. Typically the threshold will be set to a value either of two or three standard deviations outside of the mean level for a specified time interval. These have been found to be useful in clinical diagnoses.

With this understanding of the operation of the chaotic processor 14, reference is again made to the patient 12 in FIG. 1 undergoing diagnosis in accordance with this invention. As shown in FIG. 1, the air flow monitor 16 provides an input to the chaotic processor 14. It has been found that a measurement of a single cardio-respiratory function can provide sufficient data for making a diagnosis. In some situations it may desirable to use a measurement of another cardio-respiratory function exclusively of the air flow measurement or as a complement to the air flow measurement. The results from the complementary measurement could then be used to corroborate the signals from the air flow monitor. Consequently in FIG. 1 additional monitors are shown in phantom. These include an ECG 44 that measures electrical heart activity; a heart rate monitor 45 that measures heart rate; an oximeter that attaches to an individual's index finger and provides an indication of oxygen saturation levels; and a chest wall impedance monitor 47 that measures chest wall effort. Each of the monitors 44 through 47 are well known in the art. The chart recorder 50 may be included with the selector 13 to provide a real-time graphical history of the test by displaying the variations in the signal or signals being used during the diagnosis.

Figure 4A:
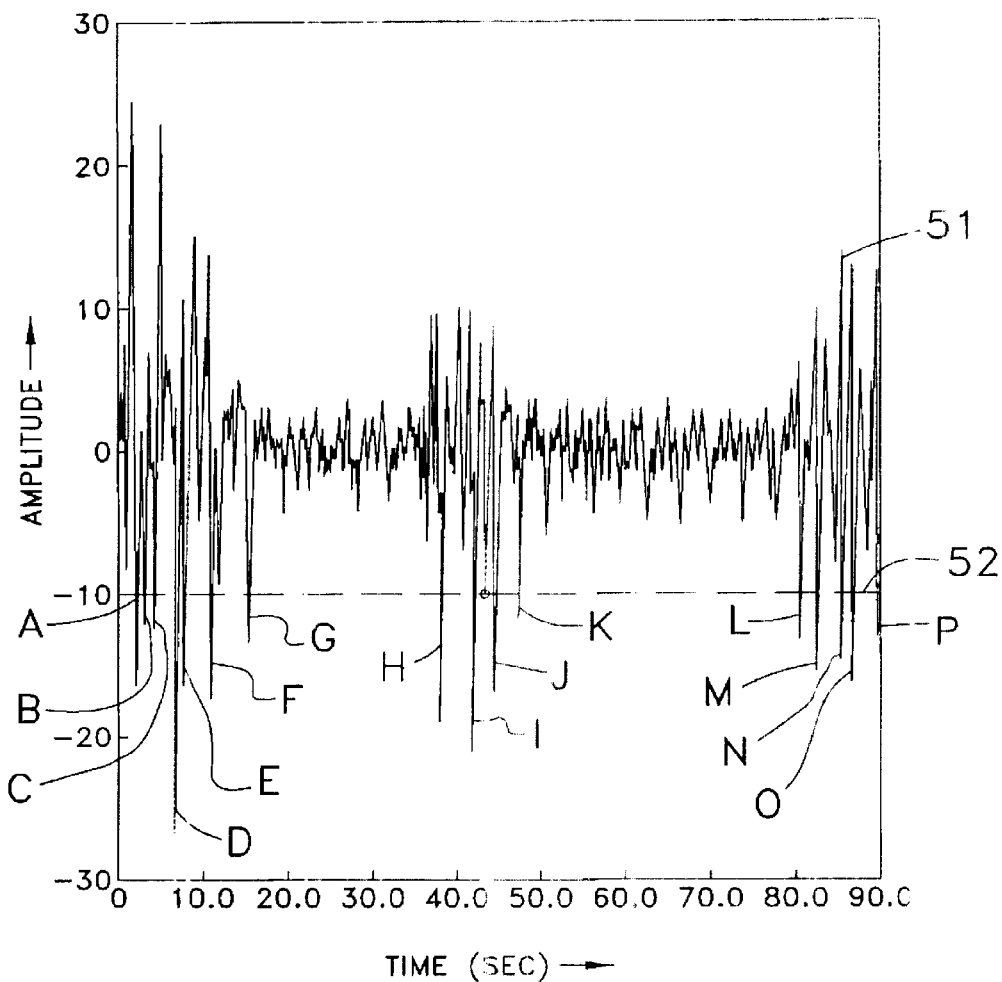
FIGS. 4A and 4B compare signals corresponding to one cardio-respiratory function when a individual is awake (FIG. 4A) and is asleep (FIG. 4B).
Figure 4B:
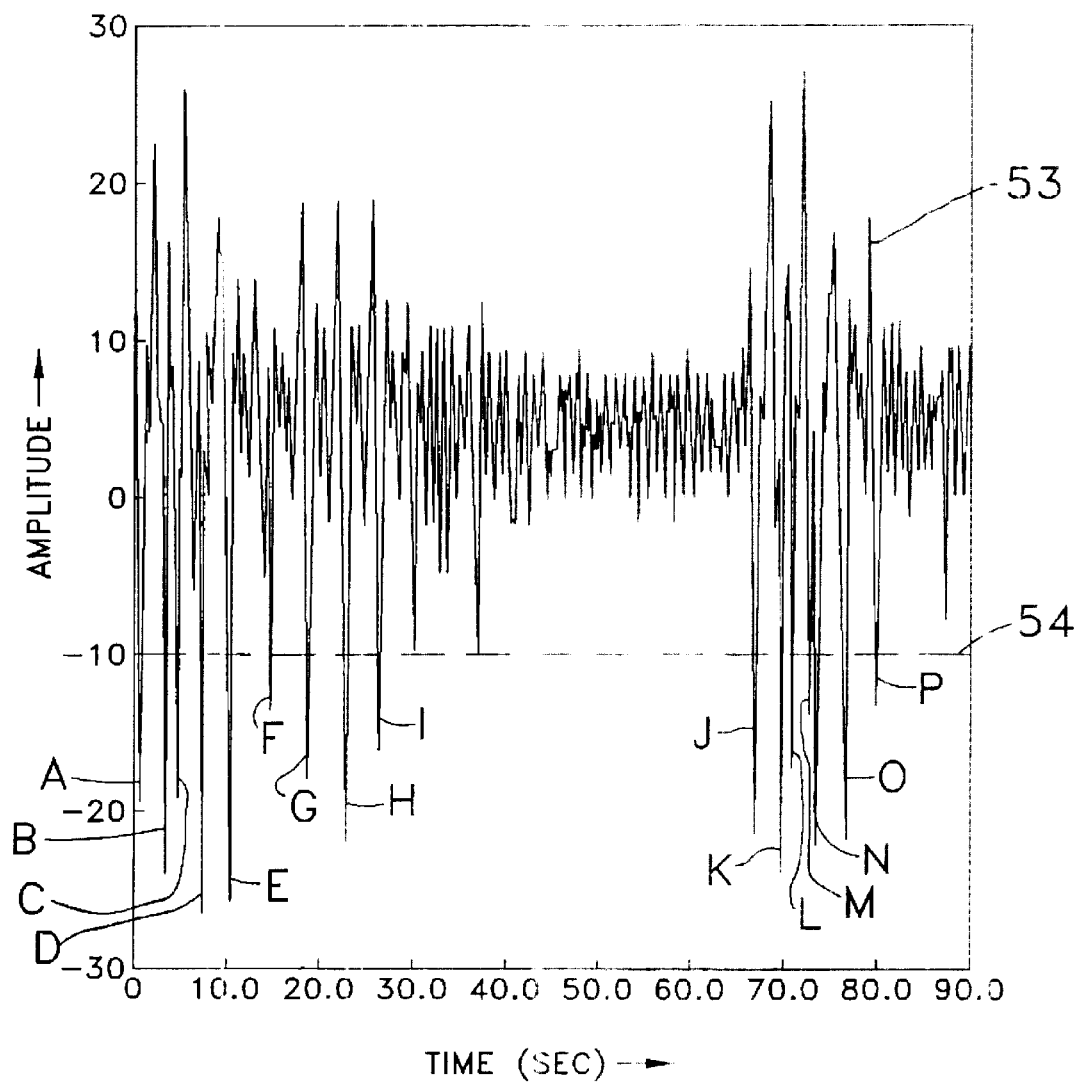

FIGS. 4A and 4B graphically compare the results of analyses made on the same patient while the patient was awake and asleep. Specifically, FIG. 4A depicts a trace 51 of the differential radius produced over a 1.5-minute test interval while the patient was awake. This data can be analyzed statistically to establish a threshold as previously described. Alternatively the threshold can be set at an arbitrary number based upon empirical information. For purposes of this explanation, it is assumed that the threshold is set at −10. FIG. 4A depicts sixteen excursions beyond the threshold represented by dashed line 52. These are identified as excursions A through P.

FIG. 4B depicts a trace 53 of the differential radial trace 53 taken from a 1.5-minute interval of a conventional sleep study. For purposes of comparison, the threshold is again set to −10 as represented by the dashed line 54. During this interval there are sixteen excursions beyond the threshold 54. They are designated as excursions A through P.

The average repetition rate of the excursions over the test interval is a key indicator of the onset of sleep apnea or other respiratory dysfunction. By comparing FIGS. 4A and 4B it will be apparent that the timing of the different excursions beyond the thresholds are different. However, the average number is statistically the same and in this particular case, exactly the same. Thus the information obtained over the 1.5-minute test interval while the patient is awake, as shown in FIG. 4A, provides the same quantitative data as the 1.5-minute interval shown in FIG. 4B obtained when the patient is undergoing a conventional sleep study.

Thus FIG. 4A provides essentially the same information in a short test while the patient is awake as when the patient is asleep for a long interval. Moreover, it has been found that the number of measurements that must be taken can be reduced. In this particular embodiment only nasal airflow was monitored, eliminating the myriad sensors utilized in conventional sleep studies. This further simplifies the diagnostic procedures. Consequently, the physical assets of a hospital that must be devoted to such a test can be significantly reduced for the test. Moreover, even assuming an interval for allowing the patient to be interviewed, prepared and tested for up to one hour, it should be possible to run 8 tests during normal working hours in the same time that would be required to conduct one sleep study after normal business hours. As a result the number of patients that can be screened at a given facility can be greatly increased over the number that can be screened using conventional sleep studies at a significantly lower cost.

Any number of available chaotic processing systems can be utilized to generate the information provided by the chaotic processor 14 shown in FIG. 1. The individual components in FIG. 1, particularly those in the processor 13 and threshold detector 40 may comprise discrete structures or software modules in a data processing system or a hybrid. The display 42 of the system in FIG. 1 can comprise a simple graphical display of the differential radius or chaotic radius over time or could superimpose either signal against a threshold. Alternatively a circuit for comparing the values of the differential chaotic radius or chaotic radius against the thresholds and automatically marking the time of such an excursion could also be produced in conjunction with the information contained in the chaotic processor 14.

This invention has been disclosed in terms of certain embodiments. It will be apparent that many modifications can be made to the disclosed apparatus without departing from the invention. For example, temperature measurements of air flow could be modified to pressure measurements of air flow to yield similar information. Therefore, it is the intent of the appended claims to cover all such variations and modifications as come within the true spirit and scope of this invention.

What is claimed is:

1. A method for diagnosing a patient for physiological respiratory dysfunction including the steps of:

monitoring a cardio-respiratory function over time while the patient is awake;

generating a time series vector representation of the monitored cardio-respiratory function;

generating a signal for the monitored function based upon chaotic processing of the corresponding time series vector representation;

establishing a threshold value for the generated signal; and identifying as a time marker each excursion of the signal beyond the threshold value.

2. A method as recited in claim 1 wherein said signal generating step includes generating a chaotic radius signal and a chaotic differential radius signal based upon chaotic and differential processing of the time series vector representations of a second cardio-respiratory function.

3. A method as recited in claim 2 wherein the cardio-respiratory function is taken from the group of cardio-respiratory functions consisting of nasal air flow pressure, oxygen saturation, chest wall impedance, heart rate and heart activity (EKG).

4. A method as recited in claim 2 wherein said generation of the differential radius signal includes:
generating an embedding delay value based upon the time series vector representation;
comparing the magnitudes of the terms of the vector representation at a given time and at a time delayed by the embedding delay value to obtain a chaotic radius; and
generating in response to each value of the chaotic radius the differential chaotic radius for the given time.

5. A method as recited in claim 4 wherein said step of determining an embedding delay includes:
converting a monitored function into a time series of samples;
generating a vector time delay interval in response to the data in the time series of samples; and
generating the time series vector representation based upon the value of the data in the time series of samples at intervals corresponding to the vector time delay interval.

6. A method as recited in claim 5 wherein said step of generating the vector time delay interval includes the step of obtaining average mutual information from the time series of samples.

7. A method as recited in claim 5 wherein said generation of the embedding delay value includes the step of obtaining global false nearest neighbor information from the time series vector representation.

8. A method as recited in claim 5 wherein said step of generating the differential chaotic radius includes comparing, at times corresponding to each vector time delay interval, the magnitude of the time series vector representation at that time and the magnitude of the time series vector representation at time offset by the embedding delay value.

9. A method as recited in claim 5 wherein:
the sampling frequency at which said time series representation is generated for the monitored function is greater than the greatest frequency of physiologic relevance with respect to the monitored cardio respiratory function;
the vector time delay is an integer multiple of the sampling interval; and
the embedding function is an integer multiple of the vector time delay.

10. A method as recited in claim 2 wherein the cardio-respiratory function is nasal air flow.

11. A method as recited in claim 10 wherein the sampling frequency is at least 10 Hz.

12. A method as recited in claim 10 wherein the sampling frequency is between 10 Hz and 40 Hz and said monitoring step occurs over an interval that is less than about one hour.

13. Apparatus for diagnosing a patient for physiological respiratory dysfunction comprising:
monitoring means for monitoring a cardio-respiratory function over time while the patient is awake;
first means for generating a time series vector representation of the monitored cardio-respiratory function;
second means for generating a signal for the monitored function based upon chaotic processing of the corresponding time series vector representation;
third means for establishing a threshold for the generated signal from said second means, said third means computing a mean level and a standard deviation of the mean level and establishing the threshold as a function of the computed standard deviation and mean level; and
marker identifying means for identifying each excursion of the signal from said second generating means beyond the threshold.

14. Apparatus as recited in claim 13 wherein said second generating means includes means for generating a chaotic radius signal and a chaotic differential radius signal based upon chaotic and differential processing of the time series vector representations of the first and second cardio-respiratory functions, respectively.

15. Apparatus as recited in claim 14 wherein said monitoring means includes at least one of a group of cardio-respiratory function monitors consisting of thermistor means for monitoring oral-nasal air flow, finger pulse oximetry monitoring means for monitoring oxygen saturation, chest wall monitoring means for measuring chest wall impedance and heart rate monitoring means for monitoring heart rate and wherein first, second and third generating means and said marker identifying means act on signals from at least one of each of said group of monitoring means.

16. Apparatus as recited in claim 15 wherein said differential chaotic radius signal generation means includes:
means for generating an embedding delay value based upon the time series vector representation;
means for comparing the magnitudes of the terms of the vector representation at a given time and at a time delayed by the embedding delay value to obtain a chaotic radius; and
means for generating, in response to each value of the chaotic radius the differential chaotic radius for the given time.

17. Apparatus as recited in claim 16 wherein said embedding delay determining means includes:
means for converting a monitored function into a time series of samples;
means for generating a vector time delay interval in response to the data in the time series of samples; and
means for generating the time series vector representation based upon the value of the data in the time series of samples at intervals corresponding to the vector time delay interval.

18. Apparatus as recited in claim 17 wherein said means for generating the vector time delay interval includes means for obtaining average mutual information from the time series of samples.

19. Apparatus as recited in claim 17 wherein said generation of the embedding delay value includes the step of obtaining global false nearest neighbor information from the time series vector representation.

20. Apparatus as recited in claim 17 wherein said means for generating the differential chaotic radius includes means for comparing, at times corresponding to each vector time delay interval, the magnitude of the time series vector representation at that time and the magnitude of the time series vector representation at time offset by the embedding delay value.

21. Apparatus as recited in claim 17 wherein said first generating means includes means for establishing a sampling frequency at which said time series representation is generated for the monitored function that is greater than the greatest frequency of physiologic relevance with respect to the monitored cardio respiratory function and wherein the vector time delay is an integer multiple of the sampling interval and the embedding function is an integer multiple of the vector time delay.

22. Apparatus as recited in claim 14 wherein said monitoring means monitors nasal air flow.

23. Apparatus as recited in claim 22 wherein said first generating means includes means for establishing a sampling frequency of at least 10 Hz and wherein the vector time delay is an integer multiple of the sampling interval and the embedding function is an integer multiple of the vector time delay.

24. Apparatus as recited in claim 22 wherein the sampling frequency is between 10 Hz and 40 Hz and said monitoring means operates over an interval that is less than about one hour.

25. A method for diagnosing a patient for physiological respiratory dysfunction including sleep apnea, the method comprising:

monitoring at least the air flow of a patient over time while the patient is awake;

generating a time series vector representation of the air flow;

generating a signal for the air flow based upon chaotic processing of the corresponding time series vector representation;

establishing a threshold value for the generated signal; and identifying as a marker each excursion of the signal beyond the threshold value.

26. A method for diagnosing a patient for physiological respiratory dysfunction including sleep apnea, the method comprising:

monitoring at least the air flow of a patient over time while the patient is awake;

generating a time series vector representation of the air flow;

generating a signal for the air flow by generating a chaotic radius signal and a chaotic differential radius signal based upon chaotic and differential processing of the time series vector representation;

establishing a threshold value for the generated signal; and identifying as a marker each excursion of the signal beyond the threshold value.

27. A method for diagnosing a patient for physiological respiratory dysfunction, the method comprising:

monitoring a cardio-respiratory function of a patient over time while the patient is awake;

generating a time series vector representation of the monitored cardio-respiratory function;

generating a chaotic radius signal and a chaotic differential radius signal based upon chaotic and differential processing of the time series vector representation of the cardio-respiratory function;

establishing a threshold value for the generated chaotic differential radius signal; and identifying as a marker each excursion of the chaotic differential radius signal beyond the threshold value.

28. An apparatus for diagnosing a patient for physiological respiratory dysfunction including sleep apnea, the apparatus comprising:

an air flow monitor for monitoring the patient's air flow over time while the patient is awake and outputting an analog air flow signal;

a chaotic processor configured to generate a time series vector representation of the air flow signal and configured to generate a differential radius signal for the air flow signal based upon chaotic processing of the time series vector representation;

a threshold selector which establishes a threshold for the differential radius signal from the chaotic processor, said threshold establishing the threshold as a function of the standard deviation and mean of the differential radius signal; and a display for identifying each excursion of the differential radius signal from the chaotic processor beyond the threshold.

29. An apparatus for diagnosing a patient for physiological respiratory dysfunction including sleep apnea, the apparatus comprising:

at least one monitor configured to output an analog signal representation of a cardio-respiratory function of the patent over time while the patient is awake;

a chaotic processor responsive to the analog signal and configured to convert the analog signal into a differential radius signal;

a threshold selector which establishes a threshold for the differential radius signal as a function of the standard deviation and mean of the differential radius signal; and a display for identifying each excursion of the differential radius signal beyond the threshold.

30. An apparatus for diagnosing a patient for sleep apnea, the apparatus comprising:

an air flow monitor configured to output an analog signal representation of the patient's air flow over time while the patient is awake;

a chaotic processor responsive to the analog signal and configured to convert the analog signal into a chaotic signal;

a threshold selector which establishes a threshold for the chaotic signal as a function of the standard deviation and mean of the chaotic signal; and a display for identifying each excursion of the chaotic signal beyond the threshold.

* * * * *